US009005165B2

(12) United States Patent
Kalser et al.

(10) Patent No.: US 9,005,165 B2
(45) Date of Patent: *Apr. 14, 2015

(54) ZERO-PRESSURE BALLOON CATHETER AND METHOD FOR USING THE CATHETER (71) Applicant: Mayser, LLC, Fort Lauderdale, FL (US)

(72) Inventors: Gary A. Kalser, Winter Park, FL (US); Gregory L. Mayback, Cooper City, FL (US); James Leone, Pittsburgh, PA (US); Matthew A. Palmer, Miami, FL (US)

(73) Assignee: Mayser, LLC, Fort Lauderdale, FL (US)

( * ) Notice: Subject to any disclaimer, the term of this patent is extended or adjusted under 35 U.S.C. 154(b) by 113 days.

This patent is subject to a terminal disclaimer.

(21) Appl. No.: 13/713,205

(22) Filed: Dec. 13, 2012

(65) Prior Publication Data
US 2013/0103005 A1 Apr. 25, 2013

Related U.S. Application Data (60) Division of application No. 12/943,453, filed on Nov. 10, 2010, now Pat. No. 8,382,708, and a continuation-in-part of application No. 11/339,258, filed on Jan. 25, 2006, now Pat. No. 7,883,503.

(51) Int. Cl.
*A61M 29/00* (2006.01)
*A61M 27/00* (2006.01)
(Continued)

(52) U.S. Cl.
CPC .......... *A61M 25/0017* (2013.01); *A61B 5/205* (2013.01); *A61B 5/412* (2013.01); *A61M 25/04* (2013.01); *A61M 25/10* (2013.01);
(Continued)

(58) Field of Classification Search
USPC ............... 604/101.01–101.05, 915–921, 544; 606/191–192, 198
See application file for complete search history.

(56) References Cited

U.S. PATENT DOCUMENTS 1,939,413 A 12/1933 Robinson
3,402,718 A 9/1968 Doherty
(Continued)

FOREIGN PATENT DOCUMENTS

JP 2002143311 A1 5/2002
WO 90/00914 2/1990
(Continued)

OTHER PUBLICATIONS

International Search Report of PCT/US10/56368 dated Jan. 14, 2011.
(Continued)

*Primary Examiner* — Rebecca E Eisenberg
(74) *Attorney, Agent, or Firm* — Mayback & Hoffman, P.A.; Gregory L. Mayback (57) ABSTRACT A safety catheter includes a shaft. The shaft has a proximal shaft portion having a proximal end, a distal tip portion defining a junction with the proximal shaft portion, a fluid drain lumen, and a balloon inflation lumen. The fluid drain lumen defines a distal fluid drain opening at the distal tip portion distal of the junction and a proximal fluid drain opening adjacent the proximal end and fluidically connected to the distal fluid drain opening. A hollow zero-pressure balloon is disposed at the junction and has an interior fluidly connected to the balloon inflation lumen, a distal leg fixedly secured to the distal tip portion, and a proximal leg temporarily secured to the proximal shaft portion.

20 Claims, 8 Drawing Sheets (51) Int. Cl.
*A61M 25/00* (2006.01)
*A61B 5/00* (2006.01)
*A61M 25/04* (2006.01)
*A61M 25/10* (2013.01)
*A61B 5/20* (2006.01)

(52) U.S. Cl.
CPC ... *A61M25/1018* (2013.01); *A61M 2025/1093* (2013.01); *A61M 25/003* (2013.01); *A61M 2025/1054* (2013.01); *A61M 2025/1065* (2013.01)

(56) References Cited

U.S. PATENT DOCUMENTS

| | | | |
|---|---|---|---|
| 3,482,576 | A | 12/1969 | Ericson |
| 3,742,960 | A | 7/1973 | Dye |
| 3,860,007 | A | 1/1975 | Binard et al. |
| 3,951,153 | A | 4/1976 | Leucci |
| 4,116,201 | A | 9/1978 | Shah |
| 4,212,192 | A | 7/1980 | Taylor |
| 4,248,214 | A | 2/1981 | Hannah et al. |
| 4,284,081 | A | 8/1981 | Kasper et al. |
| 4,384,584 | A | 5/1983 | Chen et al. |
| 4,444,185 | A | 4/1984 | Shugar et al. |
| 4,995,863 | A | 2/1991 | Nichols et al. |
| 4,998,930 | A | 3/1991 | Lundahl et al. |
| 5,066,292 | A | 11/1991 | Muller et al. |
| 5,078,681 | A | 1/1992 | Kawashima |
| 5,217,434 | A | 6/1993 | Arney et al. |
| 5,301,688 | A | 4/1994 | Stephen et al. |
| 5,378,238 | A | 1/1995 | Peters et al. |
| 5,391,148 | A | 2/1995 | Bonis |
| 5,429,620 | A | 7/1995 | Davis |
| 5,449,354 | A | 9/1995 | Konwitz et al. |
| 5,624,395 | A | 4/1997 | Mikhail et al. |
| 5,709,653 | A | 1/1998 | Leone et al. |
| 6,050,973 | A | 4/2000 | Duffy |
| 6,086,558 | A | 7/2000 | Bower et al. |
| 6,375,637 | B1 | 4/2002 | Campbell et al. |
| 6,516,216 | B1 | 2/2003 | Fontenot et al. |
| 7,186,214 | B2 | 3/2007 | Ness |
| 7,413,558 | B2 | 8/2008 | Kelley et al. |
| 7,413,564 | B2 | 8/2008 | Morris et al. |
| 7,537,580 | B2 | 5/2009 | Willard |
| 2001/0037085 | A1 | 11/2001 | Keith et al. |
| 2002/0188204 | A1 | 12/2002 | McNamara et al. |
| 2004/0147874 | A1 | 7/2004 | Kliem et al. |
| 2005/0080340 | A1 | 4/2005 | Stewart et al. |
| 2005/0197668 | A1 | 9/2005 | Lim et al. |
| 2005/0273052 | A1 | 12/2005 | Jorgensen |
| 2006/0161102 | A1 | 7/2006 | Newcomb et al. |
| 2006/0167438 | A1 | 7/2006 | Kalser et al. |
| 2006/0276746 | A1 | 12/2006 | Burnside |
| 2007/0106320 | A1 | 5/2007 | Blix et al. |
| 2007/0255209 | A1 | 11/2007 | Crooms |
| 2008/0161748 | A1 | 7/2008 | Tolkoff et al. |
| 2010/0282625 | A1 | 11/2010 | Lang |
| 2011/0071506 | A1 | 3/2011 | Gardner et al. |
| 2011/0082444 | A1 | 4/2011 | Mayback et al. |
| 2011/0152761 | A1 | 6/2011 | Mayback et al. |

FOREIGN PATENT DOCUMENTS

| | | |
|---|---|---|
| WO | 94/21951 A1 | 2/1994 |
| WO | 95/08949 | 4/1995 |
| WO | 99/45837 | 9/1999 |
| WO | 2011/060158 | 5/2011 |

OTHER PUBLICATIONS

International Search Report of PCT/US13/37909 dated Sep. 16, 2013.
Kafali, Hasan, et al.; "Expeditious Method of Urethrovesical Junction Determination in Retropubic Colposuspension with Intraballoon Illumination of Foley Catheter"; Urologia Internationalis; May 2003, vol. 70, pp. 262-264.
International Search Report of PCT/US13/59351 dated Dec. 12, 2013.
Extended European Search Report of EP Patent Application No. 10830723.2 dated Jan. 24, 2014.

ZERO-PRESSURE BALLOON CATHETER AND METHOD FOR USING THE CATHETER

CROSS-REFERENCE TO RELATED APPLICATION

This application is:
a divisional of U.S. patent application Ser. No. 12/943,453 filed on Jan. 10, 2010 (which application claims the benefit under 35 U.S.C. §119(e) of U.S. Provisional Patent Application No. 61/260,271 filed Nov. 11, 2009); and
a continuation-in-part of U.S. patent application Ser. No. 11/339,258, filed Jan. 25, 2006 (which application claims the benefit under 35 U.S.C. §119(e) of U.S. Provisional Patent Application Nos. 60/647,204 and 60/647,205, both filed Jan. 26, 2005),
the prior applications are hereby incorporated herein by reference in their entirety.

BACKGROUND OF THE INVENTION

1. Field of the Invention

The present invention relates to a catheter, especially a flexible pressure-limiting or zero-pressure balloon catheter and a method for using the catheter.

2. Description of Related Prior Art

Figure 1:
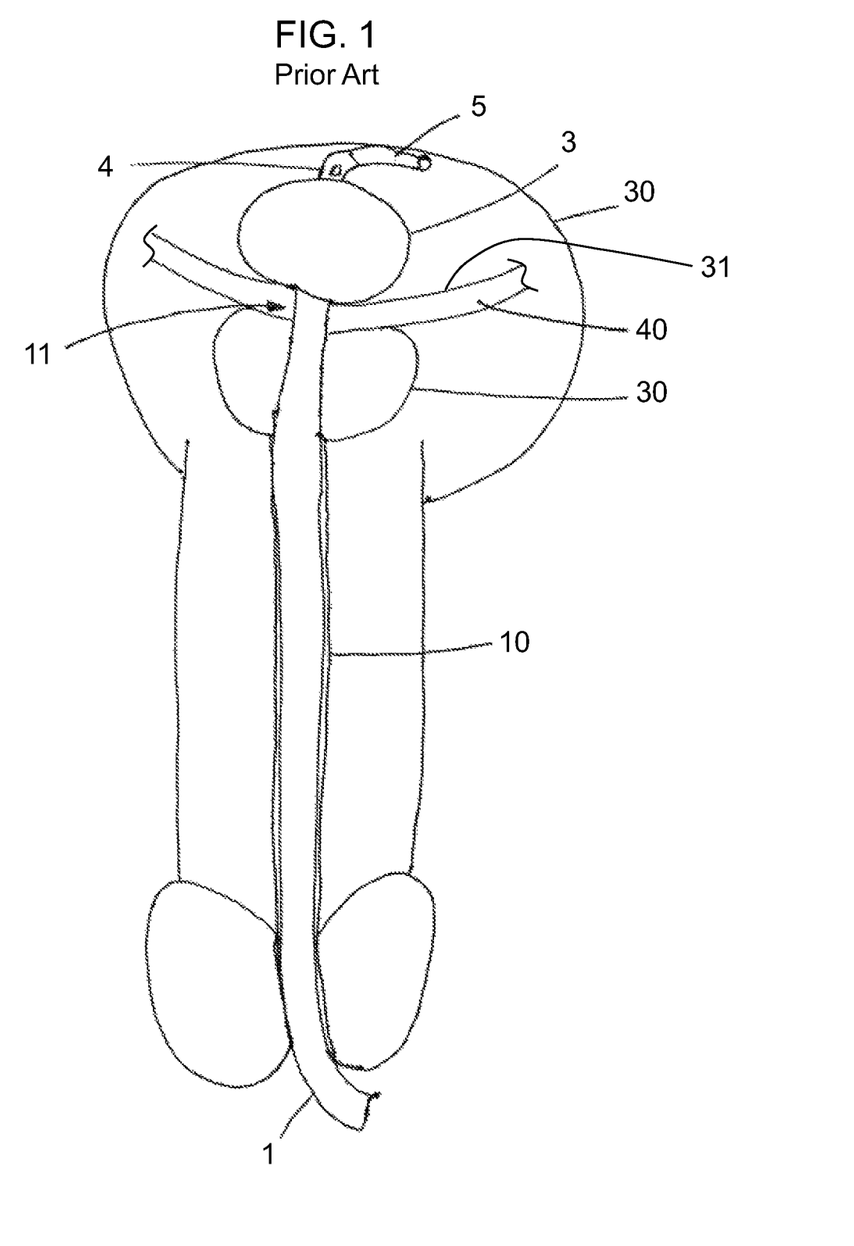
FIG. 1 is a longitudinally diagrammatic cross-sectional view of a prior art catheter ideally placed in a urethra and a bladder of a male patient.

A number of conventional balloon catheters exist in the prior art. Some catheters are used to drain the bladder of a patient during surgical procedure or to treat bladder and/or urethra or prostate conditions, for example. For example, a common balloon catheter made by RUSCH® and referred to as a Foley catheter is widely used today for treating and draining a patient's bladder. The Foley catheter is shown in FIG. 1 and has a multi-lumen shaft 1 that is disposed in the urethra 10, a balloon portion 3 disposed at the distal end of the shaft 1, a fluid drain section 4 disposed at the distal end of the balloon 3, and a curved, distal guiding tip 5 at the distal-most end of the entire catheter. When placed properly, the proximal-most side of the inflated balloon 3 rests on the interior wall 31 of the bladder 30, entirely blocking off the urethrovesical junction 11 connecting the bladder 30 and the urethra 10. In such a position, the fluid drain section 4 allows continuous drainage of the bladder 30 and the balloon 3 virtually entirely prevents the catheter from slipping out of the bladder. This ideally inserted position is shown in FIG. 1. As used herein, a fluid can be either a liquid or a gas. Exemplary fluids for inflating a balloon 3 are saline, air, or carbon dioxide gas. Exemplary fluids drained by the catheters mentioned herein include urine and blood.

Basically, the catheter has tube-like body with two lumens passing therethrough. The larger lumen 120 (see FIG. 2) is open to the bladder (distally) and empties into an ex-corporeal bag (proximally) for eventual disposal. A smaller lumen 130 is used to inflate the balloon 3 with water (typically) using a syringe attached to the inflation lumen fitting 260. When inflated in the bladder, for example, the catheter is prevented from sliding out of the urethra in use.

Over 96 million indwelling catheters are sold worldwide on an annual basis. Twenty four million catheters are sold to hospitals in the U.S. There are numerous complications associated with those catheters that need to be prevented. These complications are responsible for increases in hospital stays, excessive bleeding, mortality, as well as morbidity. They also cause an increased expense and burden on the already-stressed health care system.

The complications result from several different mechanisms. First, and probably most common, is improper placement of the catheter. Because of the unique anatomy of the male urethra, placing a urethral catheter for urinary drainage can be difficult. A problem arises when the physician, technician, or nurse thinks that the catheter is actually in a proper position when it is not. The proper position for the catheter is with the balloon located in the cavity of the bladder. In this position, the tip distal to the balloon is located in the bladder and is used to drain the bladder cavity.

For placement of this catheter in the bladder 30 in the ideal position, however, the physician or technician has no visual aid. As shown in FIG. 1, the wall 40 defining the urethrovesical junction 11 is very short in the longitudinal direction of the urethra 10. If the physician inserts the catheter too far into the bladder 30, no damage occurs from balloon inflation; however, there is a possibility of leakage around the balloon 3, which, under normal conditions, helps to lubricate the urethra 10. In such a case, gentle proximal movement will move the proximal side of the balloon 3 against the urethrovesical junction 11. The bladder 30 can then easily expand and stretch to compensate for the balloon 3. A normal bladder capacity is 400 to 500 cc. A normal balloon capacity is approximately 10 to 12 cc although larger balloons are sometimes used. A typical balloon is 5 cc, however, most clinicians put 10 cc of water in the balloon to inflate it. With 5 cc of water in the balloon, the diameter is approximately 2 cm and, with 10 cc, the diameter is approximately 2.5 cm.

The complication occurs when the technician and/or nurse inflates the balloon when the balloon is not in the bladder. If the technician does not insert the catheter in far enough, then the balloon 3 will be inflated within the urethra 10—a condition that is common and, not only is it to be avoided at all costs, is a frequent cause of bladder infections created during a hospital or clinic visit. Infections arise because inflation of the bladder 3 inside the urethra 10 causes the urethra 10 to stretch too far and tear. Even though the urethra 10 is a flexible tube, it has limits to which it can be safely stretched from within. Almost every balloon catheter has a balloon outer diameter/circumference that well-exceeds the safe stretching limit of the urethra 10. Therefore, if the balloon catheter is not inserted far enough, inflation of the balloon 3 will cause serious injury to the urethra 10. This is especially true with elderly patients who have urethra 10 that are not as elastic as younger patients. Also, just as important is the change in anatomy of older males, in particular, the prostatic portion of the urethra. With age, the prostate becomes larger and, sometimes, the catheter cannot be advanced through the prostatic portion of the urethra. When this occurs, the technician does not insert the catheter all the way into the bladder and inflates the balloon within the urethra, causing severe bleeding and damage.

The elastomeric balloon of present-day catheter products requires relatively high pressures to initiate inflation and expand to an expected full-diameter shape upon over-inflation. As such, when incorrectly placed in the urethra, the rapid inflation, combined with the high-pressure, causes the balloon to tear the surrounding membrane, called the mucosa. Tearing of the urethra 10 in this way causes bleeding and allows bacteria to enter into the bloodstream at the tear site, thus causing the subsequent bladder infection. Significant bleeding can become life threatening. The urethra can normally dilate several millimeters; however, when the balloon is inflated, this dilation is usually several centimeters. Also, without sufficient and immediate venting of the balloon inflation fluid after placement, an accidental or intentional pull on the catheter externally can and does cause extensive bodily harm to a patient fitted with the device.

Life threatening bleeds, especially in patients who are anticoagulated, can and do occur. Also when the urine is infected, as in immunocompromised patients and the elderly, the bacteria enter the blood stream and can cause serious infections (e.g., sepsis), which frequently can lead to death. If the patient survives the initial trauma, then long-term complications, such as strictures, can and usually do occur. Strictures are narrowings within the urine channel and usually require additional procedures and surgeries to correct.

Other mechanisms of catheter-induced injuries are inadvertent manipulation of the tubing or dislodging of the balloon—caused when the catheter is pulled from outside the patient due to a sudden jerk or tension. This commonly happens when the patient is ambulating or traveling from the bed to the commode or bathroom. The tubing may inadvertently become fixed while the patient is still moving, at which time a sudden jerk is imparted upon the balloon and pulls the balloon into the urethra to tear it, causing severe pain and bleeding. Injury caused by the improper, inadvertent, and/or early removal of an inflated balloon catheter is referred to as iatrogenic injury (also referred to as an in-hospital injury). Hundreds of thousands of such iatrogenic injuries occur each year—all of which need to be prevented, not only for patient safety, but also because the cost imposed on the medical health industry for each injury is enormous.

Yet another scenario occurs when the patient deliberately pulls on the catheter, thereby causing self-induced pain and injury to the urethra. This commonly happens in confused patients, for example, patients in nursing homes who have a disease or cognitive dysfunction problem, such as Alzheimer's disease, or other diseases that make the patient unable to understand the necessity of having a catheter. Confusion occurs when the patient has a spasm causing a strong urge to urinate and pain. During the spasm, the confused patient often tugs and pulls on a catheter, which results in injury. Like iatrogenic injuries, these self-induced injuries must be prevented.

The injuries mentioned herein are not limited to males and also cause severe damage to the female bladder and urethra. The injuries can also occur post-surgically, which makes the damage even more severe. One common situation where injury is caused is when the patient is medicated with morphine or other analgesics that render the patient confused and unable to make rational decisions. Feeling the foreign body inside the urethra, the confused patient does not know to leave it alone and, instead, gives it the injury-causing tug. These injuries have been well-documented and are not limited to adults. Numerous injuries are documented in pediatric patients.

Usually, it takes time to make a diagnosis of patient-caused catheter injury. Immediately after diagnosing the injury, a technician needs to deflate the catheter. However, once the urethra is torn, replacing the damaged catheter with another catheter is quite difficult and, in fact, exacerbates the injury. Sometimes, the patient has to be taken to the operating room to replace a urinary drainage tube once the injury occurs. Because catheters and leg bags are now used routinely in certain situations during home health care, this scenario is not limited to hospitals and occurs at nursing homes and patients' homes.

Most of the recent catheter technology has been focused on reducing urinary tract infections that are caused by catheters, injuries that are usually the most common catheter-related complications.

In a conventional balloon 3, the balloon 3 has a substantially constant balloon wall thickness. The balloon 3 is fixed to the outer surface of a fluid drainage line (not illustrated in FIG. 1) and is not intended to be removed therefrom or to burst thereon unless an extraordinary amount of inflation occurs. If such an event happens, the material of the balloon will open at a random location based upon the microscopic fractures or weaknesses in the material itself. Such a tearing event is not supposed to occur under any circumstances during use with a patient.

Prior art catheters are not constructed to prevent tearing of the urethra during a catheter implanting procedure and are not constructed to break in any predefined way. Accordingly, it would be beneficial to provide a balloon catheter that does not inflate past the tearing limit of a urethra and deflates in a desired, predefined way under certain conditions.

SUMMARY OF THE INVENTION

It is accordingly an object of the present invention to provide a very low or zero-inflation pressure balloon catheter and method for using the catheter that overcome the hereinafore-mentioned disadvantages of the heretofore-known devices and methods of this general type and that does not inflate when the catheter is placed, for example, in the urethra, and quickly and rapidly deflates if pulled out prior to manual deflation of the balloon.

With the foregoing and other objects in view, there is provided, in accordance with the invention, a safety catheter includes a shaft. The shaft has a proximal shaft portion having a proximal end and a distal end, a distal tip portion defining a junction with the proximal shaft portion, a fluid drain lumen, and a balloon inflation lumen. The fluid drain lumen defines a distal fluid drain opening at the distal tip portion distal of the junction and a proximal fluid drain opening adjacent the proximal end and fluidically connected to the distal fluid drain opening. A hollow zero-pressure balloon is disposed at the junction and has an interior fluidly connected to the balloon inflation lumen, a distal leg fixedly secured to the distal tip portion, and a proximal leg temporarily secured to the proximal shaft portion.

In accordance with another feature of the invention, the proximal shaft portion adjacent the junction has a given outer diameter and a portion of the junction adjacent the proximal shaft portion has an outer diameter less than the given outer diameter.

In accordance with a further feature of the invention, the distal tip portion adjacent the junction has an outer diameter less than the given outer diameter, equal to the given outer diameter, or equal to the outer diameter of the junction.

In accordance with an added feature of the invention, a proximal portion of the junction adjacent the proximal shaft portion has a given outer diameter and the proximal shaft portion adjacent the proximal portion of the junction has an outer diameter greater than the given outer diameter.

In accordance with an additional feature of the invention, the distal tip portion adjacent the junction has an outer diameter greater than the given outer diameter, equal to the given outer diameter, or equal to the outer diameter of the junction.

In accordance with yet another feature of the invention, the shaft has a length sufficient to perform urinary catheterization.

In accordance with yet a further feature of the invention, the proximal leg of the hollow balloon is relatively inflexible in relation to the distal end of the proximal shaft portion and the distal end of the proximal shaft portion and the proximal leg of the hollow balloon form a removable compression seal therebetween.

In accordance with yet an added feature of the invention, the removable compression seal has a breakaway point at a pull force of between approximately 1 pound and approximately 15 pounds applied to the proximal shaft portion, between approximately 1 pound and approximately 5 pounds applied to the proximal shaft portion, and/or between approximately 1.5 pounds and approximately 2 pounds applied to the proximal shaft portion.

In accordance with yet an additional feature of the invention, when the balloon is inflated with a fluid and a pull force of greater than approximately 15 pounds is applied to the proximal shaft portion, the compression seal exceeds a breakaway point and thereby deflates the inflated hollow balloon. The pull force can be greater than approximately 5 pounds or, in particular, greater than approximately 2 pounds.

In accordance with again another feature of the invention, the proximal leg is temporarily secured to the proximal shaft portion in an inverted orientation.

In accordance with again a further feature of the invention, the hollow balloon is operable to fold back upon itself when removed from the proximal shaft portion.

In accordance with again an added feature of the invention, the hollow balloon is operable to inflate with and withstand pressures of between approximately 0.2 atmospheres and 0.5 atmospheres without an appreciable increase in diameter.

In accordance with again an additional feature of the invention, the shaft has an internal balloon valve operable to selectively open a channel between the fluid drain lumen and the balloon interior.

In accordance with still another feature of the invention, the internal balloon valve is operable to open the channel when a pressure in the balloon is between approximately 0.3 atmospheres and approximately 1.5 atmospheres.

In accordance with still a further feature of the invention, the proximal leg of the balloon is temporarily secured at the distal end of the proximal shaft portion.

In accordance with a concomitant feature of the invention, the distal fluid drain opening is distal of the distal leg of the balloon.

The zero-pressure balloon catheter of the present invention prevents injury by having the balloon automatically deflate before an injury can occur, for example, when being forced to withdraw from the bladder or being forced to inflate within a urethra. While the catheter of the present invention makes it a safer device for urinary drainage, the present invention can also be used for any procedures in which balloons are used to occlude cavities. Examples of these procedures include coronary artery vessels and peripheral vascular vessels, such as the aorta and extremity vessels. Balloon dilations of other lumens, such as ureters and the esophagus, are also candidates for use of the catheter of the present invention.

Some of the embodiments of the present invention utilize a valve (e.g., a slit valve) that permits reuse when utilized. With embodiments having no such valve, the invention is a single use after deflation occurs. Although deflation of such a catheter renders it useless, the act of immediate deflation protects the patient from serious harm and cost of replacing a catheter is minimal as compared to the cost of treating catheter-induced injury. Prevention of such injuries is becoming more and more important because the injuries are commonplace. The increase occurs for a number of reasons. First, a greater percentage of the population is aging. Second, there is a current trend to use less-skilled health care personnel to perform more procedures and to be responsible for treatment, both of which save money. The shortage of nursing professionals (R.N.s) exacerbates this trend. The present tendency is to use nursing professionals for more functions, such as administration and delivery of medications. This leaves only the less-skilled technicians with the task of taking vital signs and inserting catheters. Under such circumstances, more injuries are likely. Lastly, catheter-related complications are becoming more severe due to the increased use of anticoagulation medication, such as PLAVIX®, that is frequently prescribed in treating cardiovascular disease.

Yet another possible complication arising from the standard Foley catheter is that the balloon will not deflate even when the deflation mechanism is activated. This situation can occur, for example, because the wrong fluid is used to inflate the balloon or when a fluid, such as saline, crystallizes, which happens occasionally. Sometimes, the ability to deflate the catheter is interrupted because the drainage channel that is used to deflate the balloon becomes obstructed, which is common if the catheter is left in place too long. Remedy of such a scenario involves an invasive procedure, which includes threading a needle or other sharp object somewhere through the body cavity to puncture the balloon and, thus, dislodge the catheter. Yet another possible complication can occur when there is a stricture evolved. A stricture is scar tissue in the urethra that impedes the passage of the catheter. In such a case, the technician sometimes uses excessive force in trying to push the catheter into the bladder, thereby causing a tear and bleeding.

With the zero-pressure auto-deflating balloon of the present invention, the technician, nurse, or doctor merely needs to pull on the catheter to cause the catheter to automatically deflate, thus sparing the patient from any additional surgical procedures.

The added benefit of the present invention is not just for safety, significant financial benefits arise as well. It is believed that catheter-induced injuries are much more common than public documentation suggests. Catheter-related trauma occurs roughly at least once a week in a large metropolitan hospital. Usually, each incident not only increases the patient's hospital stay substantially, but also the expense of the stay. Each incident (which is usually not reimbursed by insurance) can increase the cost to the hospital by thousands, even tens of thousands, of dollars.

When additional surgery is required to repair the catheter-induced injury, increased expense to the hospital is not only substantial, if litigation occurs as a result of the injury, damages awarded to the patient can run into the millions of dollars. The catheter of the present invention, therefore, provides a safer catheter that has the possibility of saving the medical industry billions of dollars.

To prevent urethra tearing occurrences due to premature-improper inflation of the balloon and/or due to premature removal of an inflated balloon, an exemplary embodiment of the invention of the instant application provides a balloon safety valve.

The maximum stress that a typical urethra can take without tearing and/or breaking is known and is referred to as a maximum urethra pressure. It is also possible to calculate how much pressure is exerted upon the exterior of a balloon of a balloon catheter by measuring the pressure required to inflate the balloon. Knowing these two values, it is possible to construct a balloon that breaks rapidly and/or ceases inflation if the maximum urethra pressure is exceeded.

For example, in a first exemplary embodiment, the balloon, which is typically some kind of rubber, silicone, or plastic, can be made with a breaking point that instantly deflates the balloon if the pressure in the balloon exceeds the maximum urethra pressure. It is acknowledged and accepted that, once the balloon breaks, this catheter is useless and must be discarded because the cost of patient injury far outweighs the cost of the disposable catheter. Also, such a balloon is limited to inflation with a bio-safe fluid to prevent unwanted air/gas from entering the patient. If, however, air or other gas will not injure the patient, the fluid can be air or another gas.

As an alternative to a one-use breaking safety valve, a multi-use pressure valve can be added to the balloon inflation lumen and can be set to open into the drainage lumen if the maximum urethra pressure exceeded in the balloon or the balloon inflation lumen. Such a valve can be located near or at the balloon inflation port. Any combination of the above embodiments is envisioned as well.

Another exemplary embodiment of the present invention provides the catheter with a balloon that inflates with virtually no pressure. As used herein, "virtually no pressure," "zero-pressure" and "low-pressure" are used interchangeably and are defined as a range of pressure between approximately standard atmospheric pressure and 0.3 atmospheres (5 psig). This is in contrast to "high-pressure," which is greater than approximately 1.5 atmospheres (22 psig). With such a configuration, the zero-pressure balloon can be deflated with virtually no force. As such, when the clinician attempts to inflate the zero-pressure balloon of the present invention within a urethra, the balloon simply does not inflate. Likewise, when the already inflated balloon within the bladder is forced into the urethra, such deflation needs virtually no pressure to collapse the balloon to fit into the urethra. In both circumstances, injury to the urethra is entirely prevented.

Although the invention is illustrated and described herein as embodied in a zero-pressure balloon catheter and a method for using the catheter, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

Before the present invention is disclosed and described, it is to be understood that the terminology used herein is for the purpose of describing particular embodiments only and is not intended to be limiting. The terms "a" or "an", as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically.

As used herein, the term "about" or "approximately" applies to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. In this document, the term "longitudinal" should be understood to mean in a direction corresponding to an elongated direction of the catheter.

BRIEF DESCRIPTION OF THE DRAWINGS

In the following, the invention will be described in more detail by exemplary embodiments and the corresponding figures. By schematic illustrations that are not true to scale, the figures show different exemplary embodiments of the invention.

DETAILED DESCRIPTION OF THE EXEMPLARY EMBODIMENTS

While the specification concludes with claims defining the features of the invention that are regarded as novel, it is believed that the invention will be better understood from a consideration of the following description in conjunction with the drawing figures, in which like reference numerals are carried forward.

Herein various embodiment of the present invention are described. In many of the different embodiments, features are similar. Therefore, to avoid redundancy, repetitive description of these similar features may not be made in some circumstances. It shall be understood, however, that description of a first-appearing feature applies to the later described similar feature and each respective description, therefore, is to be incorporated therein without such repetition.

Figure 2:
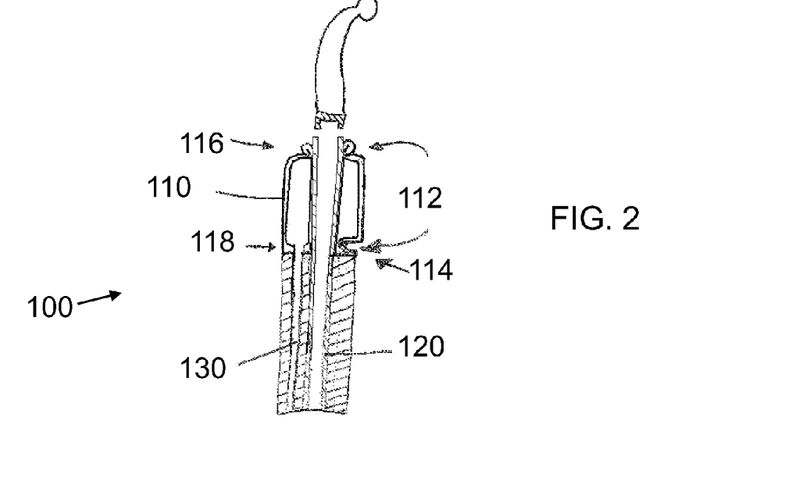
FIG. 2 is a fragmentary, enlarged, cross-sectional view of a distal portion of a first embodiment of a pressure-limiting balloon catheter according to the invention.

Referring now to the figures of the drawings in detail and first, particularly to FIG. 2 thereof, there is shown a first embodiment of a pressure-limiting balloon catheter 100 that does not inflate past the tearing limit of a lumen in which the catheter 100 is placed, for example, in the urethra.

To prevent occurrences of urethra tearing due to premature-improper inflation of the balloon and/or due to premature removal of an inflated balloon, the invention of the instant application provides the balloon 110 with a balloon safety valve 112. As set forth above, in a balloon 3 of a conventional catheter (see reference numerals 1 to 5 in FIG. 1), the high-pressure balloon 3 is fixed to the outer surface of the fluid drainage lumen 120 (not shown in FIG. 1) and is not intended to be removed therefrom or to burst thereon unless an extraordinary amount of inflation occurs. Such a tearing event is not supposed to occur under any circumstances during use with a patient. If such an event happens, the material of the balloon 3 will open at a random location, based upon the microscopic fractures or weaknesses in the material itself, and risk of serious damage to the patient is associated with the bursting, as well as a risk of balloon fragmentation, which could leave pieces of the balloon 3 inside the patient after removal of the catheter 1.

In contrast to such conventional devices, the balloon 110 of the present invention is created specifically to tear when a predefined pressure exists in or is exerted on the balloon 110. The controlled tear will occur because the balloon safety valve 112 is present. Conventional balloons have constant balloon wall thicknesses (before inflation). In contrast thereto, the balloon safety valve 112 in the first embodiment is a defined reduction in balloon wall thickness. This reduction creates a breaking point or selected breaking points at which the balloon 110 is intended specifically to break when a predefined force exists in or is imparted on the balloon 110. Because the balloon 110 is made of a material having a known tearing constant—dependent upon the thickness thereof (which is determined experimentally for different thicknesses of a given material prior to use in a patient), the balloon safety valve 112 of the present invention for urethra applications is matched to break when the pressure inside or exerted on the balloon 110 approaches the maximum urethra pressure.

In the embodiment shown in FIG. 2, a decreased thickness is formed as a first semi-circumferential groove 114 near a proximal end of the balloon 110 and/or as a second semi-circumferential groove 116 near a distal end of the balloon 110. The grooves 114, 116 can have any cross-sectional shape, including, trapezoidal, triangular, square, or rectangle, for example. Because rubber, plastic, and silicone materials tear well with thinner cuts, a relatively triangular shape or one with a narrow bottom can be an exemplary configuration. To make sure that the entire balloon 110 of the illustrated embodiment does not completely tear away from the fluid drainage lumen 120, both grooves 114, 116 do not extend around the entire circumference of the balloon 110. As shown to the left of the proximal groove 116 in FIG. 2, the groove 116 is not present on at least an arc portion 118 of the circumference of the balloon 110. The arc portion is defined to be sufficiently large so that, when the catheter 100 is removed from the patient, the balloon 110 cannot tear away entirely from the catheter 100 (and create the disadvantageous fragmentation situation as set forth above). The illustrated balloon safety valve 112 is, therefore, fashioned to keep the balloon 110 in one piece after breaking and remain firmly connected to the catheter 100 to insure that no piece of the balloon 110 will be left inside the patient after actuation of the balloon safety valve 112.

Figure 3:
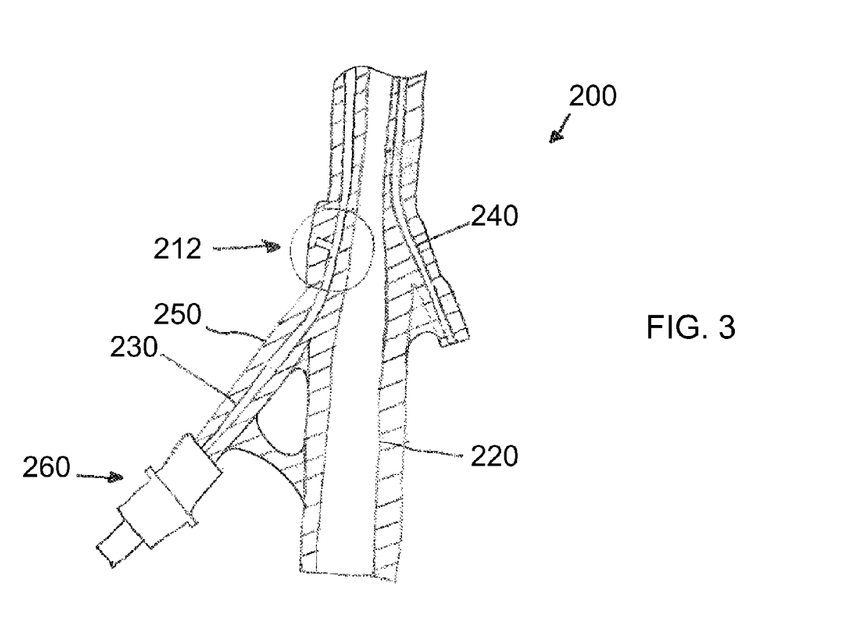
FIG. 3 is a fragmentary, enlarged cross-sectional view of a proximal portion of a second embodiment of a pressure-limiting balloon catheter according to the invention.

It is noted that the balloon 110 is inflated through an inflation lumen 130 having a proximal opening, typically formed by a female end of a luer connector (see 260 in FIG. 3). The female end is connected to a non-illustrated inflation device, for example, a distal end of a syringe for inflation of the balloon 110.

In this first embodiment, the balloon can be of rubber, silicone, or plastic, for example. Once the balloon breaks, the catheter is useless and must be discarded. Because the balloon 110 in this embodiment will break inside the patient, it should be inflated with a bio-safe fluid to prevent unwanted air, gas, or bio-unsafe fluid from entering the patient. In certain circumstances where balloon catheters are used, air or gas will not injure the patient if let out into the patient's body cavity. In such circumstances, the inflating fluid can be air under pressure, for example.

Maximum urethra pressure can also be tailored to the individual patient. Based upon a urethral pressure-measuring device, the patient's maximum urethra pressure can be measured before the catheter 100 is placed therein. A set of catheters 100 having different safety valve breaking constants can be available to the physician and, after estimating or calculating or knowing the patient's maximum urethra pressure, the physician can select the catheter 100 having a safety valve breaking constant slightly or substantially smaller than the patient's maximum urethra pressure. Accordingly, if the pressure in the balloon 110 approaches the patient's maximum urethra pressure for any reason, whether it is due to over-inflation, improper placement, and/or premature removal, the balloon 110 is guaranteed to break prior to the patient's lumen, in particular, the patient's urethra, prior to causing iatrogenic injury.

A second embodiment of the one-use breaking safety valve of a pressure-limiting balloon catheter 200 is shown in FIG. 3. The catheter 200 has a fluid drainage lumen 220, a balloon inflation lumen 230, and a secondary lumen 240.

The fluid drainage lumen 220 is connected fluidically to the body cavity (i.e., the bladder 30) for draining fluid from the body cavity.

The secondary lumen 240 can be used for any purpose, for example, for housing the radiation line that will supply energy to the radiation coil 2. It can also be used for injecting fluid into any distal part of the catheter 200 or even the body cavity itself.

The balloon inflation lumen 230 begins at a proximal end with an inflating connector 260 that, in an exemplary embodiment, is a female luer connector (of course, it can be a male luer connector too). The balloon inflation lumen 230 continues through the body of the catheter 200 all the way to the balloon 110 and is fluidically connected to the interior of the balloon 110.

Alternatively or additionally, the balloon safety valve is fluidically connected to the balloon inflation lumen 230. In a second embodiment of the safety valve 212, the valve 212 is formed integrally with the balloon inflation lumen 230 and is set to open into the environment (instead of into the patient) if the maximum urethra pressure is exceeded in the balloon 110 or the balloon inflation lumen 230. Because this safety valve 212 is located near or at the balloon inflation port 260 in this configuration, fluid used to inflate the balloon will not enter the patient when the valve 212 opens.

Figure 4:
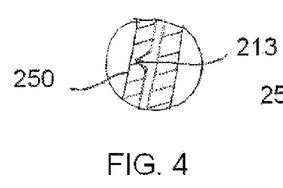
FIG. 4 is a fragmentary, enlarged, cross-sectional view of a first alternative configuration of the safety valve of FIG. 3.
Figure 5:
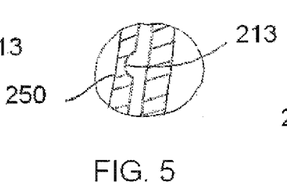
FIG. 5 is a fragmentary, enlarged, cross-sectional view of a second alternative configuration of the safety valve of FIG. 3.
Figure 6:
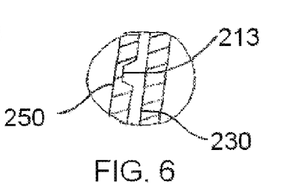
FIG. 6 is a fragmentary, enlarged, cross-sectional view of a third alternative configuration of the safety valve of FIG. 3.

The safety valve 212 in the second embodiment can merely be a narrowing of the distance between the balloon inflation lumen 230 and the outer surface 250 of the catheter 220. In FIG. 3, the valve 212 has a rectangular cross-section and extends away from the balloon inflation lumen 230. As shown in FIGS. 4, 5, and 6, respectively, the cross-section can be triangular (peaked or pyramidical in three-dimensions), curved (circular or cylindrical in three-dimensions), or trapezoidal (frusto-conical or bar-shaped in three-dimensions). The cross-sections are shown in FIGS. 3 to 7 with the narrowing emanating from the balloon inflation lumen 230 outward. As an alternative, the narrowing can begin on the outer surface of the catheter and extend inwards towards the balloon inflation lumen 230. A further alternative can have the narrowing extend from both the lumen 230 and the outer surface of the catheter.

Figure 7:
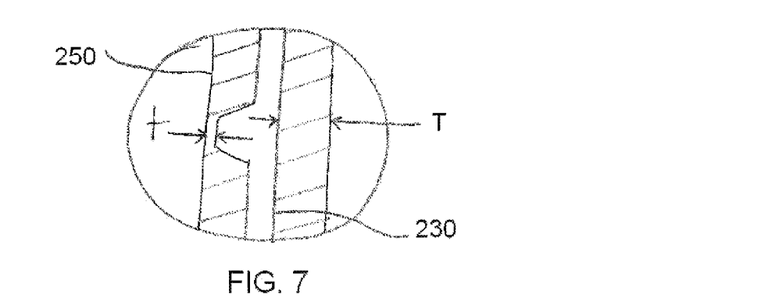
FIG. 7 is a fragmentary, further enlarged, cross-sectional view of the safety valve of FIG. 6.

The cross-sections illustrated are merely exemplary. What is important is that the thickness t between the bottom 213 of the valve 212 and the outer surface 250 of the catheter 220 in comparison to the thickness T of the catheter body over the remainder of the balloon inflation lumen 230. An enlarged view of this thickness comparison is illustrated in FIG. 7. As long as the thickness t is smaller than the thickness T ($t<T$), and as long as the force $F_b$ required to break the balloon is greater than the force $F_{sv}$ required to break the portion 213 of the safety valve 212 ($F_b>F_{sv}$), then the portion 213 of the safety valve 212 is virtually guaranteed to break every time pressure exerting a force F in the balloon inflation lumen 230 is greater than the force $F_{sv}$ required to break the safety valve ($F_{sv}>F$).

Based upon this analysis, the force $F_{sv}$ required to break the safety valve can be tuned to whatever a patient needs or a physician desires and different sized valves can be available for any procedure and provided in the form of a kit. Whether a standard maximum urethra pressure is used or a patient-specific maximum urethra pressure is measured and used, experiments can be conducted prior to use on a patient on various catheter thicknesses t to determine the pressure needed to break the portion 213 of the safety valve 212. For example, ten different maximum urethra pressures can be known as desirable setpoints and the thicknesses t can be varied such that pressure required to break the ten thicknesses correspond to the ten setpoint pressures. If, then, ten catheters are placed in such a kit, each having one of the ten thicknesses, then the physician has a range of 10 maximum urethra pressure values to use with the patient.

The safety valve 212 of the second embodiment need not be confined to the body of the catheter 200. Instead, the inflating connector 260 can, itself, be equipped with the pressure relief valve 212. Alternatively, a non-illustrated modular attachment containing the safety valve 212 can be attached to the inflating connector 260. Such a modular valve attachment is removable and replaceable (such as through a conventional luer or even a screw-threaded connection). Accordingly, as long as the catheter 200 can still be used after the valve 212 actuates (breaks), the used modular valve attachment can be replaced with a new attachment. The converse is also true for reuse of the attachment if the catheter 200 breaks and the valve of the attachment remains unbroken. A downstream end of the modular valve attachment (shaped as a luer connector) is attached removably to an upstream end of the inflating connector 260 and the upstream end of the modular valve attachment is to be connected to the balloon inflation device, which is commonly a syringe. The upstream end of the modular valve attachment is, likewise, a luer connector for easy connection to standard medical devices. In such a configuration, the safety valve 212, 312 of the present invention can be entirely separate from the catheter 200, 300 and, therefore, form a retrofitting device for attachment to any luer connector present on conventional catheters.

Figure 8:
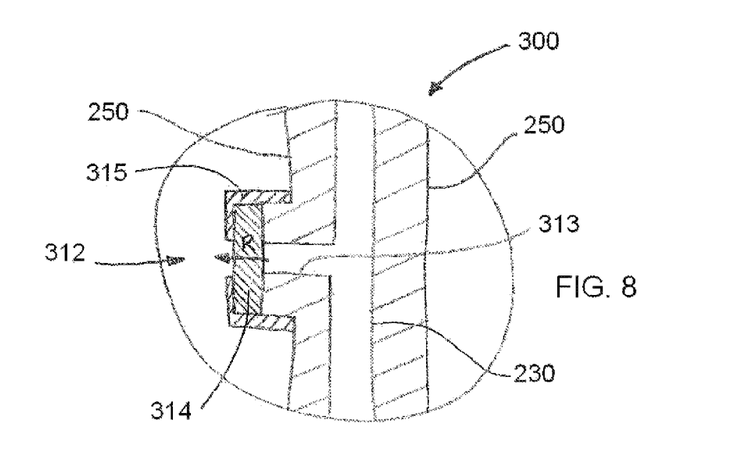
FIG. 8 is a fragmentary, further enlarged, cross-sectional view of a fourth alternative configuration of the safety valve of FIG. 3.

As an alternative to the one-use breaking safety valve of the second embodiment, a multi-use pressure valve can be used. This third embodiment of the pressure-limiting balloon catheter 300 is illustrated in FIG. 8. The catheter 300 can be the same as the catheter 200 in FIG. 3 except for the portion illustrated in FIG. 8. Instead of having a narrowing thickness t of the lumen wall, the valve portion 313 extends entirely to the environment. However, a one-way valve 314 (shown only diagrammatically in FIG. 8) is attached to the open end of the valve portion 313 and is secured to the outer surface 250 of the catheter 300 to close off the open end of the valve portion 313. The one-way valve 314 can be secured directly to the outer surface 250 (e.g., with an adhesive) or a connector 315 (e.g., a threaded cap) can secure the one-way valve 314 to the open end of the valve portion 313. Regardless of the configuration, the one-way valve 314 includes a device that does not permit fluid from exiting the lumen 230 until a given resistance R is overcome. This given resistance R can be selectable by the physician depending upon the one-way valve that is chosen for use if a set of one-way valves having different resistances R are available for use by the physician. Just like the second embodiment, the resistance R can be set to correspond to desired maximum urethra pressure values. Therefore, when used, the fluid exits the one-way valve 314 into the environment well before the patient's maximum urethra pressure is exceeded by the balloon.

The one-way valve 314 can be a mechanical one-way valve. Additionally, the one-way valve 314 can be a material having a tear strength corresponding to the desired set of resistances R. The material can be a fluid-tight fabric, a rubber, a plastic, or silicone different from the material making up the catheter. The material can even be a rubber, plastic, or silicone the same as the material making up the catheter but having a reduced thickness t than the thickness T of the catheter. Alternatively, the one-way valve 314 can be a slit valve. Various exemplary embodiments of such a valve can be found in U.S. Pat. No. 4,995,863 to Nichols et al., which is hereby incorporated herein by reference in its entirety.

Because the safety valve 212, 312 is located at the proximal end of the catheter 200, 300, the distal end of the catheter 200, 300 can take the form of a distal end of a conventional balloon catheter 2, 3, 4, 5. Alternatively, the distal end shown in FIG. 2 can also be used for redundant over-pressure protection.

Figures 9, 10:
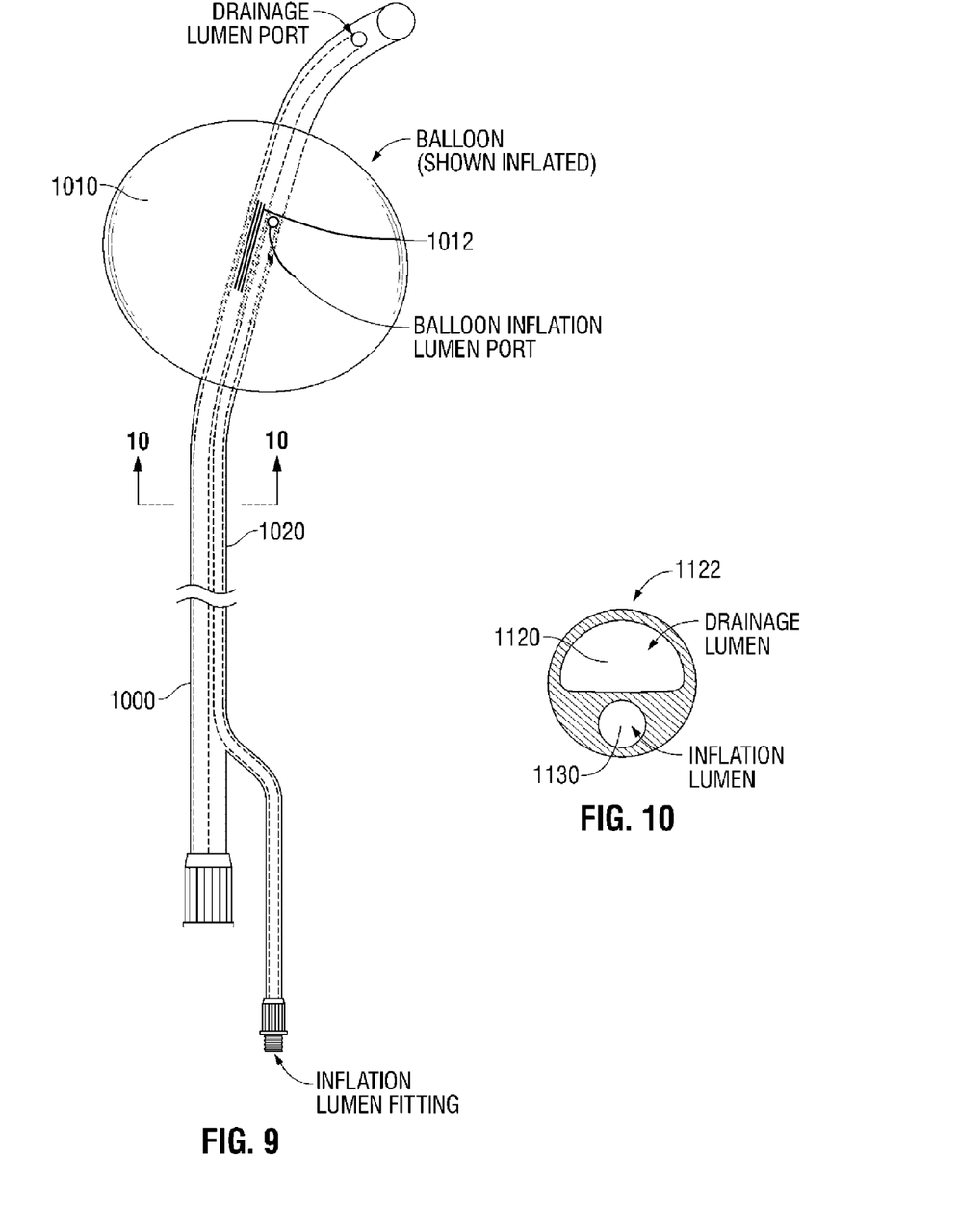
FIG. 9 is a fragmentary, partially hidden, perspective view of an exemplary embodiment of a zero-pressure safety catheter according to the invention.
FIG. 10 is a cross-sectional view of a portion of the catheter of FIG. 9 at section line 10-10.
Figure 11:
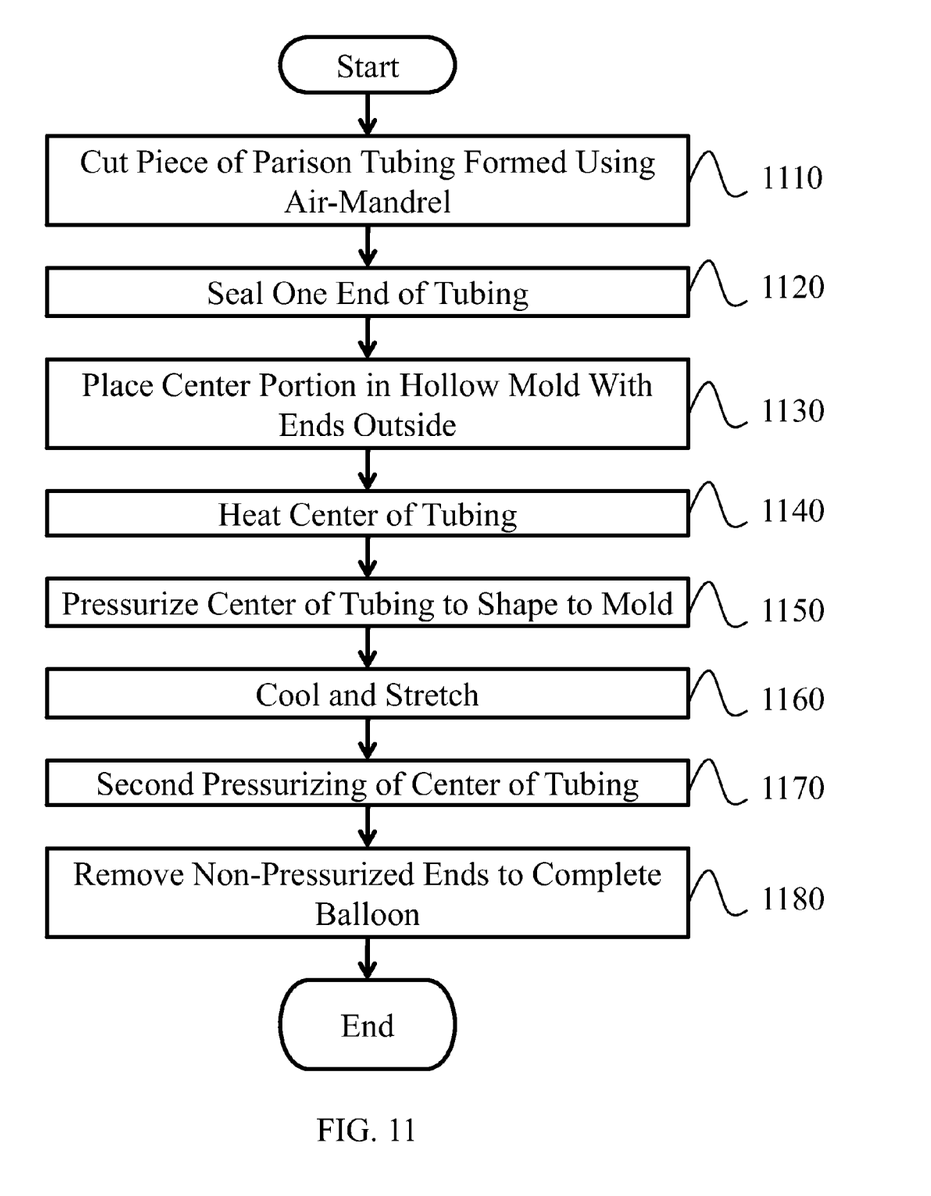
FIG. 11 is a process flow diagram of a method of forming a zero-pressure balloon according to the invention.
Figure 12:
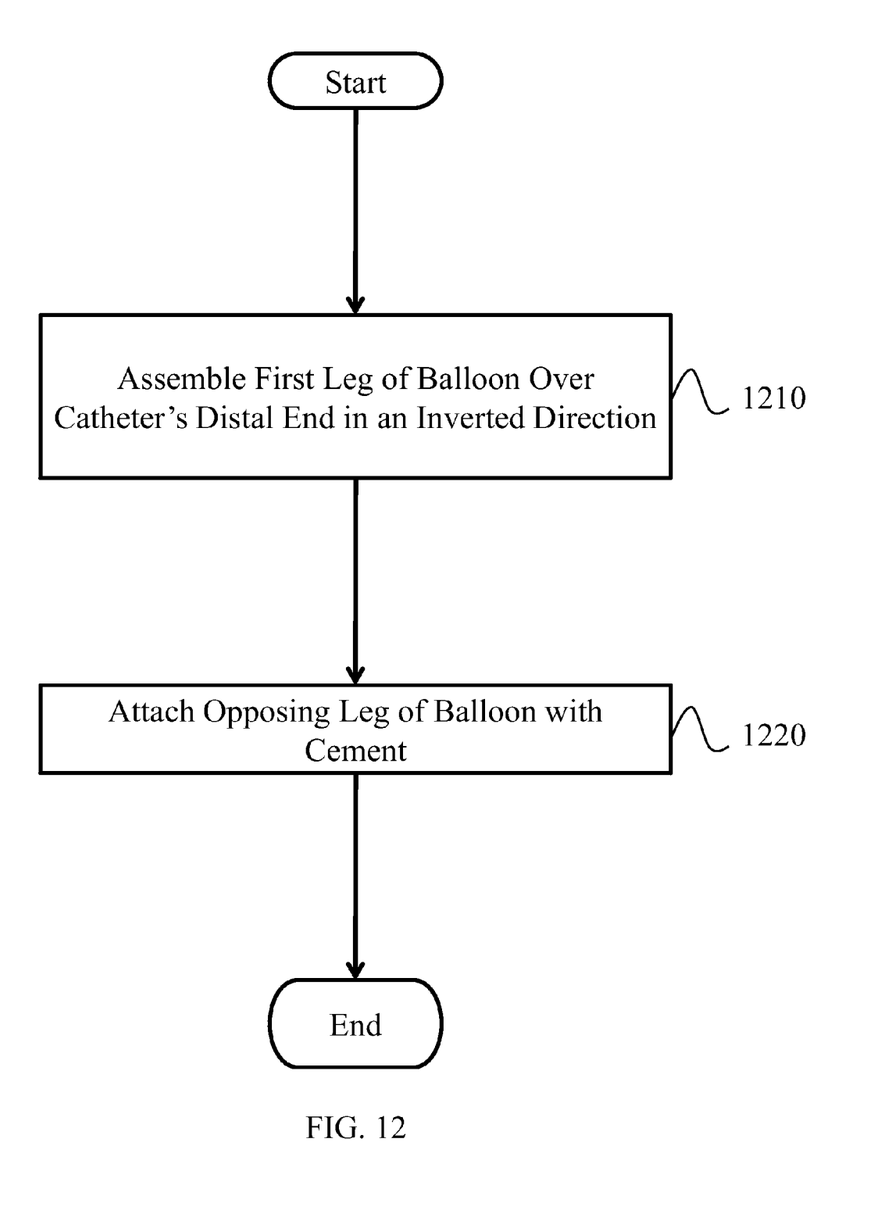
FIG. 12 is a process flow diagram of a method of attaching a zero-pressure balloon according to the invention.
Figure 13:
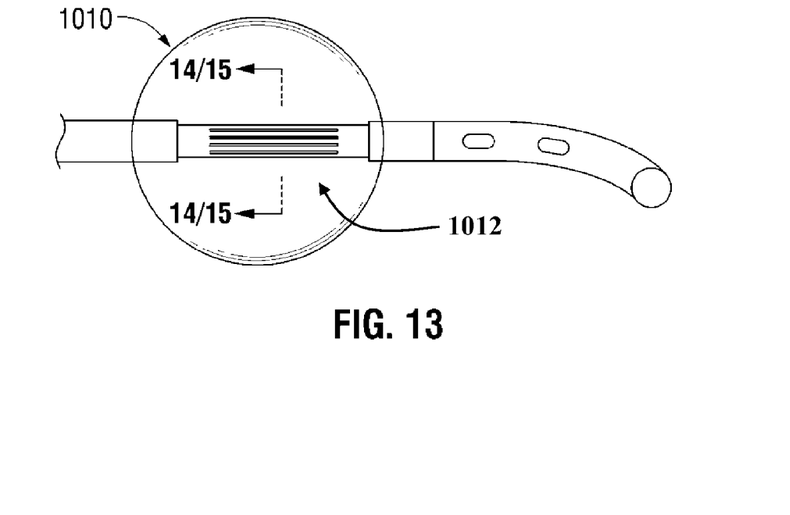
FIG. 13 is a fragmentary, enlarged, perspective view of a distal portion of an exemplary embodiment of a zero-pressure catheter according to the invention.

In another exemplary embodiment of the present invention, FIGS. 9 to 18 illustrate alternatives to the elastomeric balloon described above. In particular, the above elastomeric balloon is replaced by a thin walled, pre-formed, fixed diameter balloon 1010 that inflates with virtually no pressure and withstands pressures between approximately 0.2 atmospheres (2.9 psi) and 0.5 atmospheres (7.35 psi), the latter of which is approximately equal to the maximum urethra pressure, without an appreciable increase in diameter. Examples of such balloon materials and thicknesses are used in the medical field already, such as those used in angioplasty. Other exemplary materials can be those used in commercial (party) balloons, for example, MYLAR®, or similar materials such as nylon, PTA, PTFE, polyethylene and polyurethane, for example. In FIGS. 10 and 12, the balloon 1010 is shown in a spherical shape. However, the balloon 1010 can be, for example, cylindrical with flat or conically tapering ends.

The inflation balloon 1010 can be formed by heating a tubular material within a mold or formed by heat-sealing thin sheets to one another (e.g., party balloons have two sheets). One example of the relatively non-compliant, thin-walled balloon 1010 of the present invention is formed using a blow-molding process. In the blow-molding process, a thermoplastic material such as nylon, polyurethane, or polycarbonate is extruded or formed into a hollow, tube-like shape (parison) and is subsequently heated and pressurized, usually with air, inside a hollow mold having a shape to form the final outer dimensions of the balloon. An example of the blow molded product is the common plastic soda or water bottle containers.

One exemplary, but not limiting, process to form the zero-pressure balloon of the present invention is described with respect to FIG. 11 and includes, in Step 1110, cutting a relatively short piece of "parison" tubing that is formed using standard "air-mandrel" extrusion techniques. In Step 1120, one end of the tubing is sealed. The center portion of the tubing is placed in a hollow mold, leaving both ends extending outside of the mold, in Step 1130. The center of the tubing is heated in Step 1140 with a hot stream of air through a small hole in the center of the mold for a few seconds to soften the tubing walls within the mold. The inside of the tubing is pressurized with air in Step 1150 to stretch the tubing walls to conform with the inside dimensions of the mold. After a short cooling period, an additional stretch of the formed balloon is done in Step 1160 by pulling on the (external) parison and, after a second "blowing" in the same mold in Step 1170, is used to create a very thin-walled balloon (much less than 0.001 inches, typically, based upon the parison wall thickness and the final balloon diameter). The extra (unblown) parison tubing is then cut off from both ends in Step 1180, leaving the thin walled, relatively supple balloon and its "legs" to be mounted to the catheter as described below.

This exemplary process can be used to create thin, non-compliant balloons for "angioplasty" of blood vessels at pressures exceeding 12 atmospheres of pressure, for example. Although these pressures are not necessary in the present application, it is witness to the fact that very strong thin-walled balloons can result from the above manufacturing process.

The present invention's thin, non-compliant zero-pressure balloon can be attached to the drainage catheter in a number of ways. In a first exemplary attachment embodiment, reference is made to FIGS. 12, 13, and 16. Each of the balloon's distal and proximal legs is attached to the distal end of the drainage catheter using standard (FDA-approved) cements. The non-compliant, thin-walled balloon is dimensioned to envelop the "slit valves" shown, for example, in FIG. 13, as an exemplary configuration of the invention. The balloon's thin walls allow folding of the balloon without a significant increase in the catheter outer diameter for ease in catheter insertion.

Figure 16:
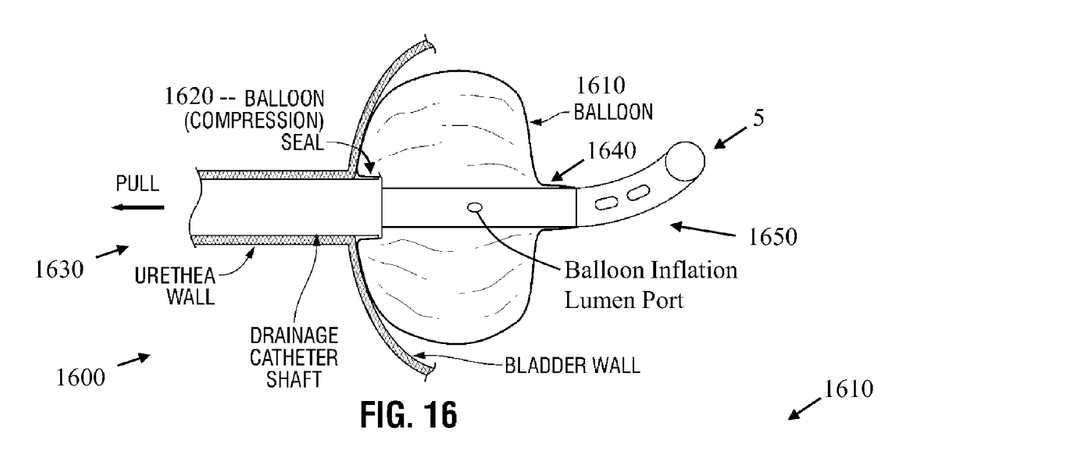
FIG. 16 is a fragmentary, enlarged, partially cross-sectional view of an everting catheter according to the invention in a correctly inserted position in the bladder.

A second exemplary, but not limiting, process to attach the zero-pressure balloon of the present invention to the safety catheter 1600 of the present invention, which can be used with or without the slit valves, is described with respect to FIGS. 12 and 16 and includes, in Step 1210, assembling a first proximal leg 1620 of the balloon 1610 over the distal end of the drainage catheter shaft 1630 in an "inverted" direction (open end toward the balloon interior as shown in FIG. 16). This inverted connection is accomplished with a mechanical release that can be formed, for example, merely by using the shape of the proximal leg 1620 of the balloon 1610 or by using a separate compression device, such as an elastic band, or by using adhesives that removably connect the proximal leg 1620 to the drainage catheter shaft 1630. In a compression only example, the proximal balloon seal is, thereby, formed by the force of the "inverted" relatively non-compliant proximal leg 1620 being extended over and around the distal end of the flexible drainage catheter shaft 1630 by, for example, stretching the silicone material of the drainage catheter shaft 1630 to reduce its outer diameter. The other, distal leg 1640 of the balloon 1610 can, then, be attached in Step 1220 using cements (as in the first example above).

To further aid in balloon assembly and catheter deflation and insertion, the outer diameter of the catheter 1600 under the balloon 1610, as well as the inner diameter of the distal balloon leg 1640, can be reduced as compared with the outer diameter of the drainage catheter shaft 1630, which configuration is shown in FIGS. 16 to 19. The reduced-diameter portion of the catheter 1000 is referred herein as the distal tip portion 1650 and extends from the distal end of the drainage catheter shaft 1630 at least to the distal end of the distal balloon leg 1640. As shown, the distal tip 5 also can have the same reduced diameter (or can be reduced further or increased larger as desired). Thus, if the outer diameter of the distal tip portion 1650 is reduced immediately distal of the proximal balloon seal 1620, any predetermined pull force will stretch the catheter shaft 1630, thereby reducing the outer diameter of the catheter shaft 1630 at the proximal balloon seal and allowing the proximal balloon leg 1620 to slide or peel distally and deflate the balloon quickly, at which time all fluid is released therefrom into the bladder or urethra, for example. It is envisioned that the proximal balloon leg 1620 can be mounted with the balloon leg 1620 in a non-inverted or "straight" position if desired with similar results. However, in such a configuration, sliding of the proximal leg 1620 over the distal end of the catheter shaft 1630 may be more resistant to a pulling force on the exposed proximal end of the catheter shaft 1630.

With a zero-pressure configuration as described and referred to herein, the balloon 1010 is under zero-pressure or low pressure. Thus, the inflation device (e.g., a syringe) need not be configured to deliver pressure much above the low pressure range described above. Mere presence of the filling liquid in the balloon, makes the balloon large enough to resist and prevent movement of the balloon into the urethra and out of the bladder without having an internal, high pressure. As such, when inserted improperly in the urethra, the balloon will simply not inflate because there is no physical space for the balloon to expand and because the inflation pressure remains beneath the urethral damaging pressure threshold. If the inflation device is configured for low pressure, even maximum delivered pressure to the balloon will be insufficient to inflate the balloon within the urethra, thereby preventing any possibility of balloon inflation inside the urethra.

In the other case where the balloon is inflated properly within the bladder but the catheter is improperly removed out from the patient without deflating the balloon, safety devices of the invention prevent tearing of the urethra upon exit. Any combination of the internal balloon valve 1012 (e.g., the slit valve of FIG. 13 formed through the wall of a portion of the drainage lumen 1120 located inside the balloon 1010) and the removable proximal balloon seal 1620 can be used; one or both can be employed to provide the safety features of the invention. In operation, when a predetermined inflation pressure is reached, the internal balloon valve 1012 opens and any fluid in the balloon 1010 is emptied through the drainage lumen 1120 into the bladder (distal) and/or the external drain bag (proximal), the latter of which is not illustrated. As set forth above, the point at which pressure causes the internal balloon valve 1012 to open is defined to be less than the pressure needed to damage the urethra when a fully inflated prior-art balloon catheter is improperly removed as described herein. In a low-pressure state, in which the balloon 1010 is filled with a fluid (either liquid or gas), there is not enough pressure to force open the internal balloon valve 1012 and permit exit of the fluid out from the balloon 1010. In a higher-pressure state (below urethra damage pressure), in contrast, pressure exerted on the fluid is sufficient to open the internal balloon valve 1012, thus permitting the fluid to quickly drain out of the balloon 1010 and into the drainage lumen 1120.

In a situation where the balloon 1010 is in the urethra and inflation is attempted, pressure exerted by the surrounding urethral wall on the inflating balloon 1010 will cause the internal balloon valve 1012 to open up well before the balloon 1010 could inflate. Thus, the balloon inflation fluid will, instead of filling the balloon 1010, exit directly into the drainage lumen 1120. In an alternative embodiment, the fluid used can be colored to contrast with urine (or any other fluid that is envisioned to pass through the drainage lumen). Thus, if the balloon 1010 is inserted only into the urethra and inflation is attempted, the inflating fluid will immediately exit into the drainage lumen and enter the exterior (non-illustrated) drain bag. Thus, within a few seconds, the technician will know if the balloon 1010 did not enter the bladder and inflate there properly. In such a situation, the technician needs to only insert the catheter further into the urethra and attempt inflation again. The absence of further colored inflation fluid in the drain bag indicates that correct balloon inflation occurred.

In the other situation where the balloon 1010 is inflated within the bladder and the catheter 100 is pulled out from the bladder without deflating the balloon 1010, pressure exerted by the urethrovesical junction 11 upon the inflated balloon 1010 will cause the valve 1012 to open up quickly and cause fluid flow into the drainage lumen 1120 before injury occurs to the junction 11 or the urethra. If, in such a situation, the catheter is also equipped with the removable proximal balloon end, then, as the removable proximal balloon end is peeling off of the proximal side, the slit valve opens up to relieve pressure either before or at the same time the peeling off occurs. This allows the inflation fluid to exit even faster than if just the valve 1012 is present.

Figure 14:
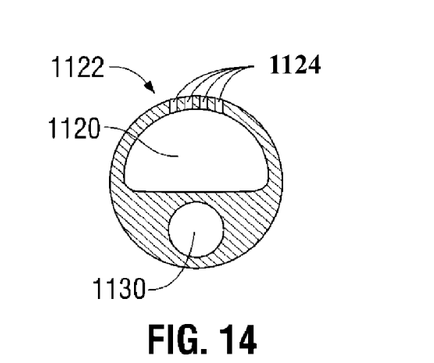
FIG. 14 is a cross-sectional view of a slit-valve portion of the catheter of FIG. 13 at section line 14-14.
Figure 15:
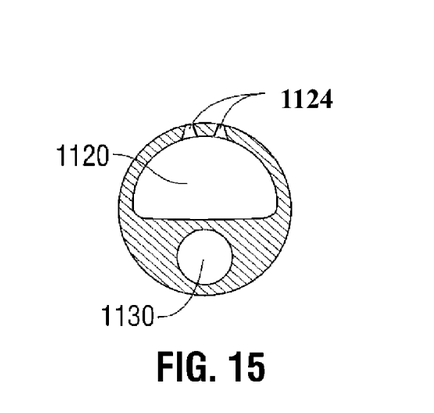
FIG. 15 is a cross-sectional view of an alternative embodiment of a slit-valve portion of the catheter of FIG. 13 at section line 15-15.

Exemplary embodiments of the internal balloon valve 1012 are illustrated in FIGS. 14 and 15. This internal balloon valve 1012 is formed by cutting the wall of the drainage lumen 1120 at the portion of the catheter within the balloon 1010. The slit can be a single cut or a plurality of cuts. Some exemplary slit valves other than those shown are described in U.S. Pat. No. 4,995,863 to Nichols et al., all of which can be utilized for the present invention. The slit-opening-pressure, therefore, can be regulated by adjusting the number, length and spacing of the slit(s) and the thickness of the drainage lumen wall 1122. For example, the length and orientation of the slit(s) 1012 determines the pressure at which it/they will open and drain the balloon inflation lumen 1130. In one particular embodiment shown in FIG. 15, the slits 1124 are cut through the elastomeric walls in a way that results in a wedge-shaped cross-section. With this wedge shape, fluid within the balloon can drain under pressure easily. The wedge can be increasing or decreasing. With the former, the edges are chamfered towards one another from the central axis of the balloon toward the exterior thereof and, with the latter, the edges are chamfered towards one another from the exterior of the balloon toward the central axis.

In another exemplary embodiment, a non-illustrated, thin-walled slitted sleeve can be disposed over the portion of the drainage catheter wall 1122 within the balloon 1010 and covering a throughbore fluidically connecting the interior of the balloon 1010 to the interior of the drainage lumen 1120. As such, pressure within the balloon 1010 will open the slit(s) of the sleeve, thereby fluidically connecting the balloon 1010 interior with the drainage lumen 1120 to transfer fluid in the balloon 1010 to the drainage lumen 1120. Each of these exemplary balloon configurations entirely prevents damage caused by improper inflation or premature removal.

Alternatively, the balloon wall itself could be modified to burst at a particular pressure to release the inflation media. This weakened section could be created by mechanical, chemical, or thermal treatment for example. Mechanical measures may be accomplished by scratching the surface and, thus, thinning the balloon wall in a particular section to cause it to burst at a pre-determined pressure or actually slicing or punching a hole in the wall and covering the area with a thinner, weaker film of material which will tear at a predetermined pressure lower than the rest of the balloon. Likewise, a chemical solvent could be applied to create the same effect as the mechanical device above by making chemical changes to the plastic molecular structure of the balloon wall and, thereby, weakening a desired section of the balloon wall. Weakening a section of the wall by heat to thereby re-orient its molecular structure (much like softening by annealing) is also possible. Therefore, the preferential tearing of the balloon wall at a predetermined internal pressure can be effected in a number of ways as exemplified by, but not limited to, the methods described above.

Figure 17:
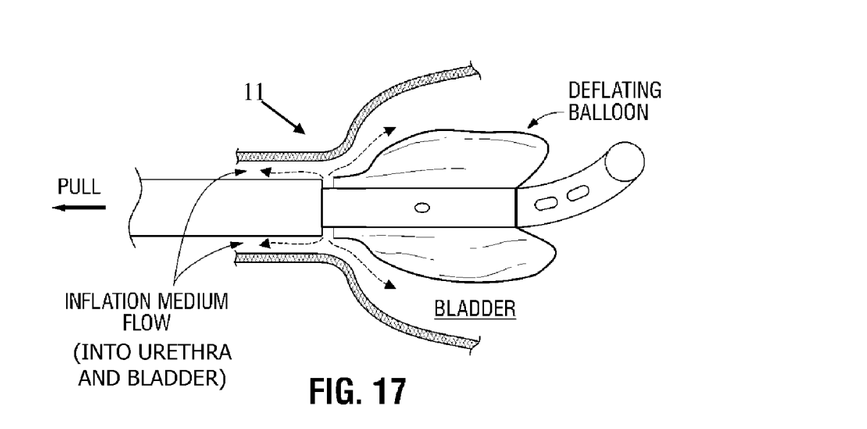
FIG. 17 is a fragmentary, enlarged, partially cross-sectional view of the catheter of FIG. 16 being pulled distally out of the bladder and beginning its everting deflation.
Figure 18:
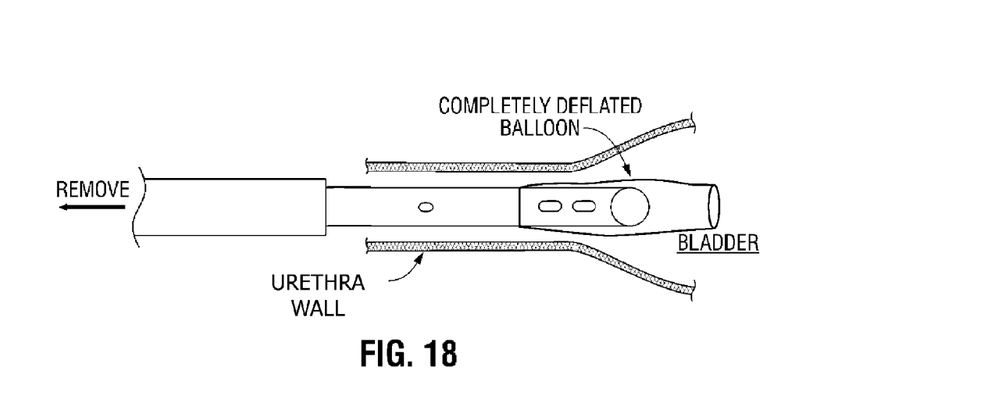
FIG. 18 is a fragmentary, enlarged, partially cross-sectional view of the catheter of FIG. 16 with the everting deflation complete.

FIGS. 16 to 18 illustrate the exemplary embodiment of the inventive catheter 1000 with the everting removable balloon 1010. These figures illustrate the situation where the balloon 1010 is inflated within the bladder and, as indicated by the pull arrow, the catheter 1000 is pulled out from the bladder without deflating the balloon 1010. Here, the distal seal 1610 of the balloon 1010 is fixed to the distal tip portion of the catheter 1000, which tip 5 has a reduced outer diameter as compared to the drainage catheter shaft 1020, and the proximal seal 1620 is removably attached (e.g., with a compression seal) to the reduced distal tip section. The pulling force causes the drainage catheter shaft to move in the proximal direction out of the urethra and, thereby, compress the proximal side of the inflated balloon 1010 against the urethrovesical junction 11. As the catheter shaft 1020 moves proximally, the force on the proximal seal 1620 increases until the seal breaks free of the catheter shaft 1020, referred to herein as the breakaway point. FIG. 17 illustrates the now partially inflated balloon 1010 just after the breakaway point occurs. Because the diameter of the distal tip portion is reduced in comparison to the distal end of the catheter shaft 1020, a gap opens up between the inner diameter of the proximal seal portion of the balloon 1010 and the outer diameter of the distal tip portion. This gap allows the inflating fluid to exit the balloon 1010 quickly into both the urethra and the bladder before injury occurs to the junction 11 or to the urethra. As the central portion of the balloon 1010 is still larger than the urethral opening of the junction 11, the friction and force imparted on the balloon 1010 causes the balloon 1010 to roll over itself, i.e., evert, until it is entirely everted as shown in FIG. 18. At this time, all of the inflating fluid is either in the urethra and/or in the bladder.

In an exemplary embodiment of the removable proximal balloon seal 1612, a pulling force in a range of 1 to 15 pounds will cause the proximal balloon seal 1612 to pull free and allow eversion of the balloon 1010, i.e., the breakaway point. In another exemplary embodiment, the range of force required to meet the breakaway point is between 1 and 5 pounds, in particular, between 1.5 and 2 pounds.

The catheter 200, 300, 1000 according to the invention can be used in vascular applications. It is known that every vessel has a tearing pressure. Balloons are used in coronary arteries, for example. If a coronary artery balloon were to burst, there would be less damage if the burst was controlled according to the invention. The same is true for a renal or iliac blood vessel. In such situations, the breakaway catheter improves upon existing catheters by making them safer. From the urinary standpoint, the breakaway balloon will not only prevent injury, but will also be a signal to the technician that he/she needs to obtain the assistance of a physician or urologist with respect to inserting the catheter.

We claim:

1. A safety catheter, comprising:
    a shaft having:
        a proximal shaft portion having a proximal end and a distal end;
        a distal tip portion defining a junction with the proximal shaft portion;
        a fluid drain lumen defining:
            a distal fluid drain opening at the distal tip portion distal of the junction; and
            a proximal fluid drain opening adjacent the proximal end and fluidically connected to the distal fluid drain opening; and
        a balloon inflation lumen;
    a hollow balloon disposed at the junction and having:
        an interior fluidly connected to the balloon inflation lumen;
        a distal leg fixedly secured to the distal tip portion; and
        a proximal leg temporarily secured to the proximal shaft portion.

2. The safety catheter according to claim 1, wherein:
    the proximal shaft portion adjacent the junction has a given outer diameter; and
    a portion of the junction adjacent the proximal shaft portion has an outer diameter less than the given outer diameter.

3. The safety catheter according to claim 2, wherein the distal tip portion adjacent the junction has an outer diameter one of:
    less than the given outer diameter;
    equal to the given outer diameter; and
    equal to the outer diameter of the junction.

4. The safety catheter according to claim 1, wherein:
    a proximal portion of the junction adjacent the proximal shaft portion has a given outer diameter; and
    the proximal shaft portion adjacent the proximal portion of the junction has an outer diameter greater than the given outer diameter.

5. The safety catheter according to claim 4, wherein the distal tip portion adjacent the junction has an outer diameter one of:
    greater than the given outer diameter;
    equal to the given outer diameter; and
    equal to the outer diameter of the junction.

6. The safety catheter according to claim 1, wherein the shaft has a length sufficient to perform urinary catheterization.

7. The safety catheter according to claim 1, wherein:
    the proximal leg of the hollow balloon is relatively inflexible in relation to the distal end of the proximal shaft portion; and
    the distal end of the proximal shaft portion and the proximal leg of the hollow balloon form a removable compression seal therebetween.

8. The safety catheter according to claim 7, wherein the removable compression seal has a breakaway point at a pull force of between approximately 1 pound and approximately 15 pounds applied to the proximal shaft portion.

9. The safety catheter according to claim 8, wherein the hollow balloon folds back upon itself when removed from the proximal shaft portion.

10. The safety catheter according to claim 7, wherein the removable compression seal has a breakaway point at a pull force of between approximately 1 pound and approximately 5 pounds applied to the proximal shaft portion.

11. The safety catheter according to claim 7, wherein the removable compression seal has a breakaway point at a pull force of between approximately 1.5 pounds and approximately 2 pounds applied to the proximal shaft portion.

12. The safety catheter according to claim 7, wherein, when the balloon is inflated with a fluid and a pull force of greater than approximately 15 pounds is applied to the proximal shaft portion, the compression seal exceeds a breakaway point and thereby deflates the inflated hollow balloon.

13. The safety catheter according to claim 7, wherein, when the balloon is inflated with a fluid and a pull force of greater than approximately 5 pounds is applied to the proximal shaft portion, the compression seal exceeds a breakaway point and thereby deflates the inflated hollow balloon.

14. The safety catheter according to claim 7, wherein, when the balloon is inflated with a fluid and a pull force of greater than approximately 2 pounds is applied to the proximal shaft portion, the compression seal exceeds a breakaway point and thereby deflates the inflated hollow balloon.

15. The safety catheter according to claim 1, wherein the proximal leg is temporarily secured to the proximal shaft portion in an inverted orientation.

16. The safety catheter according to claim 1, wherein the hollow balloon inflates with and withstands pressures of between approximately 0.2 atmospheres and 0.5 atmospheres without an appreciable increase in diameter.

17. The safety catheter according to claim 1, wherein the shaft has an internal balloon valve selectively opening a channel between the fluid drain lumen and the balloon interior.

18. The safety catheter according to claim 17, wherein the internal balloon valve opens the channel when a pressure in the balloon is between approximately 0.3 atmospheres and approximately 1.5 atmospheres.

19. The safety catheter according to claim 1, wherein the proximal leg of the balloon is temporarily secured at the distal end of the proximal shaft portion.

20. The safety catheter according to claim 1, wherein the the hollow balloon is a zero-pressure balloon.

* * * * *